US008399717B2

(12) United States Patent
Rousseaux et al.

(10) Patent No.: US 8,399,717 B2
(45) Date of Patent: Mar. 19, 2013

(54) METHOD FOR PURIFYING AN ALCOHOL FROM A FERMENTATION BROTH USING A FALLING FILM, A WIPED FILM, A THIN FILM OR A SHORT PATH EVAPORATOR

(75) Inventors: Pascal Rousseaux, Lyons (FR); Clement Cellier, Villeurbanne (FR); Frederic Ollivier, Lyons (FR)

(73) Assignee: Metabolic Explorer, Saint Beauzire (FR)

( * ) Notice: Subject to any disclaimer, the term of this patent is extended or adjusted under 35 U.S.C. 154(b) by 161 days.

(21) Appl. No.: 13/123,848

(22) PCT Filed: Oct. 2, 2009

(86) PCT No.: PCT/EP2009/062818
§ 371 (c)(1),
(2), (4) Date: Apr. 12, 2011

(87) PCT Pub. No.: WO2010/037843
PCT Pub. Date: Apr. 8, 2010

(65) Prior Publication Data
US 2011/0257441 A1    Oct. 20, 2011

(30) Foreign Application Priority Data
Oct. 3, 2008    (WO) ................. PCT/EP2008/063287

(51) Int. Cl.
*C07C 29/74*    (2006.01)
*C07C 29/76*    (2006.01)
(52) U.S. Cl. ........................................ 568/868; 568/872
(58) Field of Classification Search .................. 568/868, 568/872
See application file for complete search history.

(56) References Cited

U.S. PATENT DOCUMENTS

| | | | |
|---|---|---|---|
| 1,315,585 | A | 9/1919 | Weizmann |
| 4,420,561 | A | 12/1983 | Chen et al. |
| 4,443,542 | A | 4/1984 | Hayashida et al. |
| 4,461,012 | A | 7/1984 | Dehaene |
| 4,521,516 | A | 6/1985 | Lemme et al. |
| 4,539,293 | A | 9/1985 | Bergstrom et al. |
| 4,584,063 | A | 4/1986 | Berg et al. |
| 4,649,112 | A | 3/1987 | Datta et al. |
| 4,777,135 | A | 10/1988 | Husted et al. |
| 5,063,156 | A | 11/1991 | Glassner et al. |
| 5,254,467 | A | 10/1993 | Kretschmann et al. |
| 5,753,474 | A | 5/1998 | Ramey |
| 6,358,717 | B1 | 3/2002 | Blaschek et al. |
| 6,361,983 | B1 | 3/2002 | Ames |
| 6,428,992 | B1 | 8/2002 | Roturier et al. |
| 6,479,716 | B2 | 11/2002 | Hilaly et al. |
| 6,603,048 | B1 | 8/2003 | Corbin et al. |
| 7,056,439 | B2 | 6/2006 | Baniel et al. |
| 7,223,567 | B2 | 5/2007 | Ka-Yiu et al. |
| 7,232,664 | B2 | 6/2007 | Van Hoek et al. |
| 2004/0101479 | A1 | 5/2004 | Burbank et al. |
| 2004/0152159 | A1 | 8/2004 | Causey et al. |
| 2004/0222153 | A1 | 11/2004 | Baniel et al. |
| 2005/0069997 | A1 | 3/2005 | Adkesson et al. |
| 2005/0089079 | A1 | 4/2005 | Engel |
| 2006/0073577 | A1 | 4/2006 | Ka-Yiu et al. |
| 2007/0020740 | A1 | 1/2007 | Bennett et al. |
| 2007/0087423 | A1 | 4/2007 | Murakami |
| 2007/0178569 | A1 | 8/2007 | Leschine et al. |
| 2007/0275447 | A1 | 11/2007 | Lewis et al. |
| 2009/0155867 | A1 | 6/2009 | Soucaille |

FOREIGN PATENT DOCUMENTS

| | | |
|---|---|---|
| CN | 1522997 | 8/2004 |
| EP | 0035434 | 9/1981 |
| EP | 0146075 | 6/1985 |
| EP | 0282474 | 9/1988 |
| EP | 1 103 618 | 5/2001 |
| EP | 1103618 | 5/2001 |
| EP | 1 218 327 | 7/2002 |
| EP | 1218327 | 7/2002 |
| FR | 2583060 | 12/1986 |
| JP | 63102687 | 5/1988 |
| JP | 63254986 | 10/1988 |
| WO | 93/25696 | 12/1993 |
| WO | 2004/101479 | 11/2004 |
| WO | 2005/073364 | 8/2005 |
| WO | 2005116228 | 12/2005 |
| WO | 2006007530 | 1/2006 |
| WO | 2007041269 | 4/2007 |
| WO | 2007130518 | 11/2007 |
| WO | 2007130521 | 11/2007 |
| WO | 2007140816 | 12/2007 |
| WO | 2008018930 | 2/2008 |
| WO | 2008025522 | 3/2008 |
| WO | 2008072920 | 6/2008 |
| WO | 2008072921 | 6/2008 |
| WO | 2008074794 | 6/2008 |
| WO | 2008080124 | 7/2008 |
| WO | 2009/068110 | 6/2009 |

OTHER PUBLICATIONS

International Search Report Based on PCT/EP2009/062818 Mailed Jan. 28, 2010.
Gong et al.; "The Possibility of the Desalination of Actual 1,3-Propanediol Fermentation Broth by Electrodialysis", 2004; pp. 169-178, Desalination.
Gong et al.; "Effects of Transport Properties of Ion-Exchange Membranes on Desalination of 1,3-Propanediol Fermentation Broth by Electrodialysis", 2006; pp. 193-199; Desalination.
Green et al; "Genetic Manipulation of Acid Formation Pathways by Gene Inactivation in *Clostridium acetobutylicum* ATCC 824",— Microbiology. 1996, 142 : 2079-2086.
Soni et al.; "Continuous Acetone Butanol Fermentation : Influence of Vitamins on the Metabolic Activity of *Clostridium acetobutylicum*",—Appl. Microbiol. Biotechnol.1987.27 : 1-5.

(Continued)

*Primary Examiner* — Sikarl Witherspoon
(74) *Attorney, Agent, or Firm* — Baker Donelson Bearman Caldwell & Berkowitz, PC (57) ABSTRACT

Method for purifying an alcohol from a fermentation broth comprising adding a heavy solvent, evaporating the alcohol to be purified, and mechanically drawing out of the crystallized salts by heavy solvent flow and scrapping on a falling film evaporator, a wiped film evaporator, a thin film evaporator or a short path evaporator.

16 Claims, 4 Drawing Sheets

OTHER PUBLICATIONS

Papanikolaou et al, "The Effect of Raw Glycerol Concentration on the Production of 1,3-Propanediol by *Clostridium butyricu*", Sep. 3, 2004, pp. 1189-1196, vol. 79, Journal of Chemical Technology and Biotechnology.

Abbad-Andaloussi et al., "Properties of Allyl Alcohol-Resistant Mutants of *Clostridium butyricum* Grown on Glycerol"; 1996; p. 3499-3501, vol. 62, No. 9, Applied and Environmental Microbiology.

Gonzalez-Pajuelo et al., "Metabolic Engineering of *Clostridium acetobutylicum* for the Industrial Production of 1,3-Propanediol From Glycero", pp. 329-336, 2005; vol. 7, Metabolic Engineering.

Xiu et al.; "Present State and Perspective of Downstream Processing of Biologically Produced 1,3-Propanediol and 2,3-Butanediol"; 2008; vol. 78; pp. 917-926.

International Search Report Based on International Application No. PCT/EP2009/062818 Mailed Jan. 28, 2010.

METHOD FOR PURIFYING AN ALCOHOL FROM A FERMENTATION BROTH USING A FALLING FILM, A WIPED FILM, A THIN FILM OR A SHORT PATH EVAPORATOR

CROSS REFERENCE TO RELATED APPLICATIONS

This application is a §371 National Stage Application of PCT/EP2009/062818 filed Oct. 2, 2009, which claims priority PCT/EP2008/063287 filed Oct. 3, 2008.

The present invention relates to the purification of an alcohol from a fermentation broth.

The production of alcohol by microbial fermentation has many advantages. For example, the production of butanol, 1,3-propanediol and 1,2-propanediol by fermentation are well known. The raw starting material in the fermentation medium can be glycerol. In particular, the synthesis of 1,3-propanediol by fermentation of glycerol by clostridium has been described. The synthesis of 1,3-propanediol by fermentation of glycerol provides a significant reduction in production costs compared to chemical synthesis using petroleum products.

The production of alcohols by fermentation is often accompanied by the production of organic acids. Thus, the production of 1,3-propanediol by microbial fermentation can be accompanied by the co-production of other products or by-products, acetone in particular, or acids in the form of an acid or acetate salt.

Thus, the alcohol produced by fermentation must be purified from the fermentation broth. In addition to the alcohol, the fermentation broth may contain valuable by products (for example acetone or acetate) which may also be purified from the broth. However, the fermentation broth usually also contains impurities or unwanted by-products such as water, organic impurities, mineral salts and organic salts.

In the specific case of 1,3-propanediol, organic impurities responsible for 1,3-propanediol's colour and odour are often observed. These impurities have not been identified but it is possible that they may occur due to 1,3-propanediol degradation. Such degradation must thus be avoided during the production and purification of 1,3-propanediol.

One major problem encountered during the purification of alcohols from fermentation broths is the elimination of salts. These salts are typically sodium chlorides and calcium chlorides but also ammonium and phosphate salts. If not eliminated, these salts would precipitate during alcohol purification.

Various methods for purifying 1,3-propanediol from fermentation broths have been described, notably EP 1 218 327, U.S. Pat. No. 7,056,439, EP 1 103 618 and WO 2004101479.

U.S. Pat. No. 5,254,467 describes fermentative production of 1,3-propanediol. After elimination of the biomass, the 1,3-propanediol is purified using various techniques. Water, low-boiling and high-boiling constituents may be removed by evaporation.

With regard to salts, most notably it has been proposed to eliminate salts upstream from the purification method by various techniques such as the use of ion-exchange resins (WO 2004101479), electrodialysis (Gong et al., 2006; Gong et al., 2004) and precipitation-filtration (U.S. Pat. No. 6,361, 983).

ZHI-LONG XIU et al. relates to downstream processing of biologically produced 1,3-propanediol and 2,3-butanediol. In this review paper, various techniques are discussed including evaporation, liquid-liquid extraction and distillation techniques. ZHI-LONG XIU et al. acknowledge that desalination and deprotonization are required before distillation. One of the methods proposed is to add ethanol to provoke precipitation of salts and proteins which are then removed prior to further purification.

WO 2009/068110 describes a method for purifying an alcohol from a fermentation broth. In these methods, the addition of glycerol to the concentrated fermentation broth prevents crystallization of salts at the bottom of distillation columns. The addition of glycerol retains salts in the liquid phase until the end of the purification process. A major drawback of this process is that the amount of glycerol required to dissolve salts may be very high, leading to high purification costs.

WO 2004/101479 is also related to the purification of biologically-produced 1,3-propanediol. The purification process comprises filtration, ion exchange purification and a distillation procedure comprising at least two distillation columns. Salts are removed at the start of the process using ion exchange resins. A major problem is the fouling of the ion exchange resins, which is due to the heavy impurities of the filtrated fermentation broth. Ion exchange is an efficient technique but it leads to very high operation costs due to the need for regeneration of the resin, when the technique is applied to solutions having a high salt content. Fouling of the ion exchange resin due to the heavy impurities and quick saturation due to high salts content both lead to elevated operation costs because regeneration and/or replacement of the resin are frequently required.

US 2004/0222153 discloses a process for the recovery of 1,3-propanediol from a fermentation broth based on liquid-liquid extraction. Liquid-liquid extraction relies on extraction of 1,3-propanediol in an organic solvent. An adequate solvent is selected so that 1,3-propanediol has greater affinity for the solvent than for water. However, the limiting factor is that 1,3-propanediol is very hydrophilic and therefore a huge volume of solvent is required to extract the 1,3-propanediol efficiently.

Therefore, none of these techniques produce satisfactory results.

The present invention proposes a novel method for purifying an alcohol, such as 1,3-propanediol, from a fermentation broth. The methods of the present invention provide efficient desalinisation of the fermentation broth prior to further purification of the alcohol.

Advantageously, the methods of the present invention prevent degradation of the alcohol during the purification steps.

The methods of the present invention are based on the addition of a heavy solvent to the fermentation broth wherein the heavy solvent has a boiling point which is higher than the boiling point of the alcohol produced by fermentation. In the methods according to the invention, after addition of a heavy solvent, the fermentation broth is fed to a falling film evaporator, a wiped film evaporator or a short path evaporator wherein the alcohol is evaporated and the salts crystallize and are drawn out by the heavy solvent. The addition of the heavy solvent leads to mechanical drawing-out of the salts together with a high yield of the desired product in the distillate, thus leading to the early elimination of salts from the fermentation broth containing the alcohol to be purified.

Following removal of the salts, the alcohol may be further purified using various techniques such as for example distillation. Remaining impurities may be further removed by ion exchange or adsorption but these techniques are used as polishing techniques to reach an even higher final quality. Fouling of the ion exchange resins or of the adsorbent solid is reduced because salts and heavy impurities have been removed beforehand.

Advantageously, the methods according to the present invention make it possible to efficiently eliminate salts during the purification of an alcohol from a fermentation broth using a simple, cheap and easily industrialized process.

Advantageously, glycerol is used both for production of the alcohol and as the heavy solvent in the methods for purification the alcohol. Thus, glycerol recovered after purification of the alcohol may be recycled for production of alcohol by fermentation.

In a preferred embodiment, the invention relates to the purification of 1,3-propanediol obtained by fermentation of glycerol.

Advantageously, the methods of the present invention prevent degradation of the 1,3-propanediol during purification.

Advantageously, the methods according to the present invention prevent the appearance of the impurities responsible for 1,3-propanediol colour and odour.

According to another advantage of the present invention, the methods of this invention provide improved yield.

SUMMARY OF THE INVENTION

The present invention is related to a method for purifying an alcohol from a fermentation broth, comprising the following steps:
- a) clarifying the fermentation broth in order to obtain an aqueous solution containing the alcohol,
- b) adding a solvent to the aqueous solution to reach a proportion of solvent of at least 10% per weight, wherein the solvent has a boiling point which is higher than the boiling point of the alcohol to be purified,
- c) feeding the aqueous solution containing the solvent to a falling film evaporator, a wiped film evaporator, a thin film evaporator or a short path evaporator, for evaporation of the alcohol to be purified and drawing out of crystallized salts by the solvent,
- d) recovering the alcohol.

Preferably, the alcohol to be purified from the culture broth is 1,3-propanediol.

Preferably, clarification of the fermentation broth in step a) is carried out by filtration.

More preferably, filtration consists in successive microfiltration, ultrafiltration and/or nanofiltration steps.

In preferred embodiments, the methods of the present invention comprise removal of water from the aqueous solution containing the alcohol obtained in step a).

Preferably, in step b) of the methods according to the invention, a solvent is added to reach a proportion of at least 10% by weight of the aqueous solution, more preferably in a proportion ranging from 10% to 20% by weight of the aqueous solution.

Advantageously, the solvent added to the aqueous solution is glycerol.

In preferred embodiments, the solvent is a hydrophilic solvent and in step c) an evaporated product containing the alcohol and a bottom product containing hydrophilic solvent, salts and residual alcohol, are obtained.

Preferably, the hydrophilic solvent and the residual alcohol contained in the bottom product are recycled.

In preferred embodiments, recycling of the hydrophilic solvent and of the residual alcohol comprises the following steps:
- adding a hydrophobic solvent to the bottom product containing hydrophilic solvent, salts and residual alcohol, to reach a proportion of hydrophobic solvent of at least 5% per weight, wherein the hydrophobic solvent has a boiling point which is higher than the boiling point of the hydrophilic solvent,
- feeding the product of the preceding step to a falling film evaporator, a wiped film evaporator or a short path evaporator, for evaporation of the hydrophilic solvent and the residual alcohol and drawing out of crystallized salts by the hydrophobic solvent, wherein an evaporated product containing hydrophilic solvent, residual alcohol and hydrophobic solvent is obtained;
- decanting of the evaporated product to obtain a first phase comprising the hydrophilic solvent and the residual alcohol and a second phase comprising the hydrophobic solvent;
- recycling of the first phase comprising the hydrophilic solvent and the residual alcohol.

The hydrophobic solvent is advantageously added to reach a proportion ranging from 50% to 200% by weight of the bottom product.

It is preferred that the hydrophobic solvent is composed of rapeseed oil methyl esters (RME).

The methods of the present invention may comprise further purification of the alcohol recovered in step d).

Preferably, further purification of the alcohol comprises removing by distillation products and/or azeotropes which have a boiling point lower than that of the alcohol to be purified; and removing by distillation products and/or azeotropes having a boiling point higher than that of the alcohol to be purified.

Advantageously, further purification of the alcohol comprises removing water by evaporation.

Advantageously, further purification of the alcohol comprises ion exchange and/or adsorption.

In one embodiment the present invention relates to a method for purifying an alcohol from a fermentation broth, comprising:
- a) filtering the fermentation broth in order to obtain an aqueous solution containing the alcohol,
- b) adding a heavy solvent to the aqueous solution if the aqueous solution obtained in step a) does not already comprise a heavy solvent in a proportion of at least 5%,
- c) evaporating the alcohol to be purified and drawing out of the crystallized salts by the heavy solvent on a falling film evaporator, a wiped film evaporator or a short path evaporator, purification and recovery of the alcohol.

In another embodiment the present invention relates to a method for purifying an alcohol from a fermentation broth comprising the following steps:
- a) filtering the fermentation broth in order to obtain an aqueous solution containing the alcohol,
- b) eliminating water from the aqueous solution,
- c) optionally, adding a heavy solvent to the aqueous solution if the aqueous solution obtained in the previous steps does not already comprise a heavy solvent in a proportion of at least 5%,
- d) evaporating the alcohol to be purified and drawing out of the crystallized salts by the heavy solvent on a falling film evaporator, a wiped film evaporator or a short path evaporator,
- e) purification and recovery of the alcohol.

In another embodiment the present invention relates to a purification method comprising at least the following steps:
- a) filtering the fermentation broth in order to obtain an aqueous solution containing the alcohol,
- b) eliminating water from the aqueous solution, c) optionally, adding a heavy solvent to the aqueous solution if the aqueous solution obtained in the previous steps does not already comprise a heavy solvent in a proportion of at least 5%,
d) evaporating the alcohol to be purified and drawing out of the crystallized salts by the heavy solvent on a falling film evaporator, a wiped film evaporator or a short path evaporator,
e) eliminating products and eventually azeotropes having a boiling point lower than that of the alcohol to be purified by distillation,
f) eliminating products and eventually azeotropes having a boiling point higher than that of the alcohol to be purified by distillation,
g) purification and recovery of the alcohol.

Preferably, in the methods according to the invention, filtration of the fermentation broth consists in successive microfiltration, ultrafiltration and/or nano filtration steps.

Preferably, water is eliminated from the aqueous solution by evaporation.

In a preferred embodiment, the alcohol to be purified from the culture broth is 1,3-propanediol.

Advantageously, the heavy solvent added to the aqueous solution is glycerol.

Preferably, glycerol is added in a proportion of up to 100% by weight of the aqueous solution, preferably in proportions ranging from 5%, 10% to 20% by weight of the aqueous solution.

Preferably, the glycerol added undergoes preliminary treatment by a strong anion-exchange resin in order to eliminate any anions from the glycerol. Advantageously, in the methods of the present invention, after recovering the alcohol, glycerol is recovered.

DETAILED DESCRIPTION OF THE INVENTION

The invention thus relates to the purification of an alcohol from a fermentation broth. "Alcohol" means a molecule with at least one alcohol function. Preferably, the alcohol to be purified is a diol or a heavy alcohol. The terms "heavy alcohol" refer to an alcohol that is less volatile or has a higher boiling point than water.

Preferentially, the alcohol is selected from 1-butanol, 1,3-propanediol and 1,2-propanediol, or any other alcohol that is less volatile than water. More preferentially, the invention relates to the purification of 1,3-propanediol from a fermentation broth.

Advantageously, the raw material used in the production of alcohol by fermentation is glycerol.

Thus, the invention most notably relates to the purification of 1,3-propanediol from a fermentation broth, 1,3-propanediol can, for example, be produced by the fermentation of glycerol. Such fermentation leads to the co-production of acetone, sodium acetate and ammonium acetate. The fermentation broth obtained after fermentation contains typically water, 1,3-propanediol, glycerol, mineral and organic salts of the carboxylate type. The noble products to be recovered are 1,3-propanediol and acetone (or the acid in the form of acids or acetate salts). Acetone can be recovered according to known techniques such as stripping the solution with carbon dioxide or distillation.

A major problem is the separation of the alcohol produced by fermentation, such as 1,3-propanediol, from the mineral and organic salts contained in the fermentation broth.

In contrast to alcohols produced by other processes, alcohols produced by fermentation contain a high concentration of organic and mineral salts.

The term "salt" means any mineral or organic salt present in the fermentation broth, main mineral salts include ions such as $Na^+$, $K^+$, $Cl^-$, $SO_4^{2-}$ and $PO_4^{3-}$.

The present invention relates to a method for removing salts from a fermentation broth after fermentative production of an alcohol. The methods of the present invention also relate to further purification of the alcohol after removal of mineral and organic salts.

Another object of the present invention is the efficient purification of an alcohol from an aqueous solution containing mineral and/or organic salts.

Purification of an alcohol from a fermentation broth, for example, 1,3-propanediol by techniques such as distillation and evaporation leads to the crystallization of the mineral and organic salts which is an obstacle to the further purification of the alcohol. Various attempts have been made to remove mineral and organic salts from the fermentation broth prior to further purification of the alcohol. In distillation methods, crystallization of salts at the bottom of the distillation column is a common problem, other methods such as ion exchange lead to quick fouling of the ion exchange resin due to the high amount of mineral salts and organic salts present in the fermentation broth.

Typically, an object of the present invention is the separation of the alcohol from sodium chlorides, calcium chlorides, ammonium and phosphate salts.

In preferred embodiments, the present invention relates to the purification of an alcohol from a fermentation broth.

In a first embodiment, the present invention relates to a method for purifying an alcohol from a fermentation broth, comprising the following steps:
a) clarifying the fermentation broth in order to obtain an aqueous solution containing the alcohol,
b) adding a solvent to the aqueous solution to reach a proportion of solvent of at least 10% per weight, wherein the solvent has a boiling point which is higher than the boiling point of the alcohol to be purified,
c) feeding the aqueous solution containing the solvent to a falling film evaporator, a wiped film evaporator, a thin film evaporator,
d) or a short path evaporator, for evaporation of the alcohol to be purified and drawing out of crystallized salts by the solvent,
e) recovering the alcohol.

Fermentation may optionally be stopped by addition of a base to the fermentation broth. A base is added, for example, in the form of soda, potash or ammonia with the purpose of stopping bacterial activity. The pH achieved is between 7.5 and 14.

The first step of the alcohol purification method consists in clarification of the fermentation broth to eliminate insoluble elements, most notably large molecules, biomass, proteins and all suspended particles. Preferably, all molecules having a molecular weight over 200 Da are eliminated by clarification. Any convenient method may be used for clarification of the fermentation broth.

In preferred embodiments, clarification of the fermentation broth is carried out by filtration, "Filtration" refers to a membrane separation method. Advantageously, filtration consists successively of microfiltration, ultrafiltration and nanofiltration steps. Preferably, the clarification step consists of microfiltration and ultrafiltration. More preferably, the clarification step consists of microfiltration.

After clarification of the fermentation broth, water may be removed prior to further purification of the alcohol. Any appropriate method may be applied to remove water from the aqueous solution. Preferably, water is removed by evaporation.

The purification method further includes a step of adding a heavy solvent to the aqueous solution obtained by clarification of the fermentation broth. The terms "heavy solvent" refer to a solvent that is less volatile or has a higher boiling point than the alcohol to be purified from the aqueous solution. Alternatively, the heavy solvent is added directly to the fermentation broth. For example, if glycerol is used for production of the alcohol by fermentation, excess glycerol may be directly added during the fermentation step. Afterwards, the excess glycerol will play the role of the heavy solvent during purification of the alcohol.

Any solvent, with a boiling point higher than the boiling point of the alcohol to be purified from the aqueous solution, may be used. The solvent may be a hydrophilic or a hydrophobic solvent.

Preferably, solvents used in the methods of the present invention are selected from alcohols, fatty acid alkylmethyl (or ethyl) esters, vegetable oils or hydrocarbons. Preferably, fatty acid alkyl esters are fatty acids methyl esters.

Alcohols are selected from polyols, such as glycerol, trimethylolpropane, 1,4 butanediol, 1,2,6 hexanetriol. The preferred alcohol is glycerol.

Fatty acid alkyl esters are preferably selected from stearic, myristic, linoleic, linolenic, oleic, palmitic, or lauric acid alkyl esters, or mixtures thereof. The alkyl group constituting the ester is preferably selected from methyl, ethyl or butyl groups.

Vegetable oils such as castor oil, rapeseed oil, palm oil or linseed oil may also be used as a solvent in the methods of the present invention. Preferred are methyl, ethyl or butyl esters of rapeseed oil.

Most preferably, the solvent added to the aqueous solution is glycerol.

Preferably, the solvent, such as glycerol for example, is added to reach a proportion of at least 5%, 10%, 20%, 30%, 40%, 50%, 60%, 70%, 80%, 90% to 100% by weight of the aqueous solution. It is preferred that the heavy solvent, such as glycerol for example, is added to reach proportions ranging from 10 to 40% by weight of the aqueous solution and it is even more preferred that the heavy solvent, such as glycerol for example, is added to reach proportions ranging from 10% to 30%, preferably from 10% to 20% by weight of the aqueous solution.

In some embodiments, the solvent is used as the starting product during fermentation. After consumption of the solvent during fermentation, more solvent is added to perform the purification of the alcohol. The amount of solvent added is adjusted depending on the amount of solvent remaining in the fermentation broth. The amount of residual solvent present in the fermentation broth will depend on the rate of consumption of the solvent. However, after fermentation the solution usually contains less than 10%, preferably, less than 5% and more preferably less than 2% of solvent.

The solvent, in particular glycerol, may contain sodium chloride in solution as well as other ions. Thus it may be advantageous to pre-treat the solvent beforehand in order to eliminate some of the ions, preferably anions by means of an anion-exchange resin.

After addition of the solvent to the aqueous solution, the aqueous solution is fed to a falling film evaporator, a wiped film evaporator, a thin film evaporator or a short path evaporator.

The evaporated product contains most of the alcohol. Preferably, the evaporated product contains at least 75%, 80%, 90% or at least 95% of the alcohol.

The evaporated product typically comprises mostly water, alcohol and small amount of solvent and may also comprise some liquid impurities. The bottom product contains salts; these salts have crystallized upon evaporation of the alcohol and have been drawn out mechanically by the solvent flow and by the scraper of the evaporator. Most mineral and organic salts are removed during this evaporation step performed in the presence of the solvent in a proportion of at least 5%, preferably at least 10% per weight of the aqueous solution containing the alcohol. Typically sodium chlorides, calcium chlorides, ammonium salts, phosphate salts and other salts are separated from the alcohol at this step. The bottom product also contains the heavy solvent and may also comprise some residual alcohol, which has not been evaporated. The residual alcohol amounts usually to less than 10% and preferably to less than 5% of the alcohol of the aqueous solution.

In preferred embodiments, the alcohol is 1,3-propanediol and the solvent is glycerol. In such embodiments, passage through a falling film evaporator, a wiped film evaporator, a thin film evaporator or a short path evaporator typically leads to evaporation of water, acetone, 1,3-propanediol and of a minor fraction of the glycerol. The evaporated product may also comprise some impurities.

Evaporation takes place under atmospheric pressure, more advantageously under vacuum. Preferably, evaporation is carried out under low pressure, preferably between 0.1 and 200 mbar, more preferably between 1 and 50 mbar. Heating temperature is set to maximize evaporation yield of the alcohol.

For purification of 1,3-propanediol, temperature is set between 50° C. and 250° C., preferably between 100° C. and 150° C.

Any evaporator allowing mechanical drawing out of the salts with the solvent may be used in the present invention. The amount of solvent needed to draw out salts at the bottom of the evaporator will strongly depend on the technology of the evaporator and/or of the technology of the wiper in the case where the evaporator is a mechanically agitated evaporator. In a preferred embodiment of the invention, a falling film, a wiped film, a thin film or a short path evaporator is used. Most preferably, a wiped film, thin film or short path evaporator will be used, to minimize the amount of solvent needed to draw out the salts at the bottom of the evaporator.

Advantageously, vacuum i.e. low pressure evaporation is used. A substantial decrease of the boiling temperature of the alcohol is obtained by reducing the operating pressure. Thus, degradation of the alcohol is prevented.

A successful evaporation step will provide both a high yield of alcohol in the evaporated product, and sufficient liquid bottom product to efficiently draw out the salts. If the content of heavy solvent in the aqueous solution containing the alcohol is too low, either some alcohol will be lost as a liquid bottom product to ensure salts drawing out, or the liquid bottom product won't be sufficient to prevent fouling by the salts. Sufficient heavy solvent is added prior to the evaporation in order to obtain both a high yield of alcohol in the evaporated product and an efficient drawing out of the salts by the heavy solvent.

If sufficient solvent is added prior to evaporation, it is possible to evaporate 100% of the alcohol present in the aqueous solution. However, this is not preferred because it would also require evaporation of a significant amount of heavy solvent.

Although the evaporated product contains most of the alcohol, it is preferred that some residual alcohol is recovered in the bottom product. The residual alcohol in the bottom product of the evaporator may amount to at least 1%, 2%, 5% or 10% of the alcohol of the aqueous solution. This residual alcohol present in the bottom product after evaporation may also be recovered as described below. In that way, close to 100% of the alcohol is recovered in two successive evaporation steps. The fact that less than 100% of the alcohol is evaporated in the first evaporation step also avoids contamination of the evaporated alcohol with impurities which remain in the bottom product.

One skilled in the art will be able to set the amount of solvent to allow adequate evaporation as described above.

After removal of salts by drawing them out mechanically with the heavy solvent in an appropriate evaporator, the alcohol is recovered from the evaporated product and may be further purified. The alcohol can be further purified according to any known alcohol-purification technique, in particular by distillation. Advantageously, both topping and stripping are performed.

Optionally, an ion exchange step and/or adsorption step may also be included in the distillation sequence, as a polishing step, to maximize final product quality. These methods are well known to the skilled person and described in the literature.

Another optional step of the method of the present invention is adjusting the pH to a pH>7 during purification. By raising the pH, acids can be separated and eliminated as ions.

In preferred embodiments, the method according to the present invention also comprises removal of water leading to concentration of the evaporated product containing the alcohol to be purified. Water can be eliminated by various techniques known to persons skilled in the art.

Preferably, water is removed by evaporation. Preferably, evaporation is carried out under reduced pressure, preferably between 1 to 50 mbar, more preferably between 1 to 30 mbar. Temperature is set to vaporize 5 to 90% of the water. Preferably, temperature is set to vaporize 70, 80 to 90% of the water. Under these operating conditions, light impurities such as organic acids (acetic acid and butyric acid) are also eliminated during the evaporation of water.

Preferably, further purification of the alcohol is performed by distillation techniques. Elimination by distillation of products with a boiling point lower than that of the alcohol to be purified and products with a boiling point higher than that of the alcohol to be purified is carried out according to conventional techniques known to persons skilled in the art. Preferably, the distillation steps are performed at a pressure below 75 mbar. During topping, products with a boiling point lower than that of the alcohol to be purified are most notably water and organic acids. During stripping, products with a boiling point higher than that of the alcohol to be purified are most notably the heavy solvent, a solvent fraction less volatile than the alcohol to be purified, and residual salts not eliminated by the previous evaporation step.

Once most of the salts have been removed, purification may be carried out using techniques well known to the skilled person. The different purification steps may be performed in a different order and additional purification steps may be performed to improve the purity of the end product.

In some embodiments, an ion exchange step and/or adsorption step may be performed in between the different distillation steps or after the final distillation step. These techniques are used as a final polishing step, in order to maximize product quality.

As discussed above, ion exchange is an efficient technique for the removal of salts from various solutions. However, the removal of high salt concentration requires frequent regeneration or renewal of ion exchange resins and is linked to high operation costs.

In the methods of the present invention, the majority of organic and mineral salts are removed by crystallization and drawing out of the salts by the solvent during evaporation of the alcohol.

Ion exchange may be used primarily to remove residual ionic impurities. Fouling of the resin is thus reduced, avoiding frequent regeneration and/or replacement of the ion exchange resins and preventing high operation costs. In the methods of the present invention, so-called ion exchange resins may further be used for the removal of other impurities. For example, ion exchange resins may be used for adsorption of various organic impurities.

Ion exchange is a well-known technique and may be carried out with any suitable resin. In preferred embodiments, ion exchange resins are selected from strong anion exchange resins, weak anion exchange resins, strong cation exchange resins and weak cation exchange resins, or mixtures thereof, e.g. well known mixed-bed type ion exchange resins. The ion exchange step may consist in a treatment on any combination of the above-mentioned ion exchange resins.

Further purification of the alcohol may further comprise adsorption of impurities on adsorbent solids. The term "adsorption" refers to the collection of impurities onto the surface of an adsorbent solid, This adsorption step allows removal of impurities, which are bound to the adsorbent solid by chemical or physical attraction.

In the methods of the present invention, activated charcoal or other solid adsorbents are used to remove color-forming or odor-forming impurities from the purified alcohol. As discussed above, ion exchange resins may also be used for adsorption of such impurities. In preferred embodiments, adsorption and/or ion exchange are performed after distillation, thus reducing fouling of the solid adsorbent and minimizing costs.

In preferred embodiments, an ion exchange step and/or adsorption step is performed at the end of the distillation sequence, to produce pure alcohol from distilled alcohol. Depending on the resin or adsorbent used, addition of water to the distilled alcohol may be needed to prevent degradation of the resin or adsorbent solid degradation and/or to decrease viscosity, thus increasing mass transfer coefficients and adsorption efficiency. At this stage, water may have to be added in proportions ranging from 1 and 100%, more preferably from 10 and 20%.

In preferred embodiments, after recovering the alcohol from the evaporated product, the heavy solvent is recovered from the bottom product. The solvent is recovered, regenerated and then recycled into the purification process or into the fermentation process. Another advantage of solvent recovery is that residual alcohol, which has not been evaporated during the first evaporation step, will be recovered and recycled, thus improving the alcohol recovery yield of the whole process. The solvent may be recovered according to any suitable method and then recycled in the purification method. Preferably, the solvent is recovered by filtration, distillation or by using another falling film or thin film evaporating step with a less volatile solvent.

Preferably, the solvent used in the first evaporation step is a hydrophilic solvent such as glycerol. This first evaporation step performed in a falling film evaporator, a wiped film evaporator, a thin film evaporator or a short path evaporator allows removal of the majority of salts. After evaporation an evaporated product is obtained containing most of the alcohol and a bottom product containing the hydrophilic solvent, salts and some residual alcohol, which has not been evaporated. When a hydrophilic solvent is used in the first evaporation step, the hydrophilic solvent and the residual alcohol may advantageously be recovered and recycled into the process by adding a hydrophobic solvent to the bottom product and by performing a second evaporation step in falling film evaporator, a wiped film evaporator, a thin film evaporator or a short path evaporator.

In a preferred embodiment, the methods of the present invention further comprise the following steps:

- adding a hydrophobic solvent to the bottom product containing hydrophilic solvent, salts and residual alcohol, to reach a proportion of hydrophobic solvent of at least 5% per weight, wherein the hydrophobic solvent has a boiling point which is higher than the boiling point of the hydrophilic solvent;
- feeding the product of the preceding step to a falling film evaporator, a wiped film evaporator, a thin film evaporator or a short path evaporator, for evaporation of the hydrophilic solvent and of the residual alcohol and drawing out of crystallized salts by the hydrophobic solvent, wherein an evaporated product containing hydrophilic solvent, residual alcohol and hydrophobic solvent is obtained;
- decanting of the evaporated product to obtain a first phase comprising the hydrophilic solvent and the residual alcohol and a second phase comprising the hydrophobic solvent;
- recycling of the first phase comprising the hydrophilic solvent and the residual alcohol.

Any hydrophobic solvent, which is less volatile than the hydrophilic solvent, may be used to recover the hydrophilic solvent and the residual alcohol from the bottom product.

Hydrophobic solvents include alkyl esters preferably selected from stearic, myristic, linoleic, linolenic, oleic, palmitic, or lauric acid alkyl esters, or mixtures thereof. The alkyl group constituting the ester is preferably selected from methyl, ethyl or butyl groups. Advantageously, the hydrophobic solvent is composed of rapeseed oil methyl esters (RME).

Preferably, the hydrophobic solvent is added to reach a proportion of at least 5% by weight of the bottom product, preferably to reach a proportion ranging from 50% to 200% by weight of the bottom product.

For the recovery of the hydrophilic solvent and of residual alcohol from the bottom product, the hydrophobic solvent is added to reach a proportion ranging from 5% to 500% of the bottom product. Preferably, the hydrophobic solvent is added to reach a proportion of at least 5%, 10%, 20%, 50%, 100%, 200%, 300%, 400% or at least 500%. More preferably, the heavy solvent is added in proportions ranging from 50% to 200% of the bottom product.

Upon evaporation, a fraction of the hydrophobic solvent may be vaporized. The evaporated product contains hydrophilic solvent, residual alcohol and hydrophobic solvent. As described above, the residual alcohol is a minor fraction of the alcohol initially present in the fermentation broth. Likewise, the hydrophobic solvent that may vaporize during the second evaporation step represents a minor fraction of the hydrophobic solvent.

Preferably, the hydrophilic solvent and the residual alcohol are easily separated from the hydrophobic solvent by decantation. Hydrophobic solvent is thereby recycled from the condensed vapors. A first phase comprising the hydrophilic solvent and the residual alcohol, and a second phase comprising the heavy solvent, are obtained.

This first phase comprising the hydrophilic solvent and residual alcohol is recycled into the process. In particular, the recycled products (hydrophilic solvent and alcohol) may be added as solvent to the clarified fermentation broth at step b) of the methods described above.

After this second evaporation step in a falling film, a wiped film, a thin film or a short path evaporator, hydrophobic solvent and salts are recovered at the bottom of the evaporator. Advantageously, the hydrophobic solvent is recycled by washing the product recovered at the bottom of the evaporator with water to recover salts in the aqueous phase followed by separation of the two liquid phases. The salt depleted hydrophobic solvent is then recycled into the process.

FIGURES

FIG. 3: Method for purifying 1,3-propanediol by adding a hydrophilic less volatile solvent than 1,3-propanediol to mechanically draw out crystallized salts in a falling film or wiped film evaporator, and by recycling the hydrophilic solvent with a second evaporation step: (1) Mixing of the hydrophilic solvent with a salts-rich mixture containing 1,3-propanediol (a). The hydrophilic solvent is brought by both fresh product (b) and recycled stream (k) (2) Evaporation on a falling film or wiped film: 1,3-propanediol, light products and a small fraction of the heavy products are recovered in the distillate (d) where as salts crystallize in the evaporator and are drawn out mechanically at the bottom of the evaporator (e) by hydrophilic solvent flow and scraping (3) Mixing of salts-rich stream (e) with a hydrophobic heavy solvent which is less volatile than the hydrophilic solvent. The hydrophobic solvent is brought by both fresh product (f) and recycled streams (g) and (h). (4) Evaporation on a falling film or wiped film: residual 1,3-propanediol and hydrophilic solvent are recovered in the distillate (j) where as salts crystallize in the evaporator and are drawn out mechanically at the bottom of the evaporator (l) by hydrophobic solvent flow and scraping. (5) Separation of the two liquid phases, to recycle both hydrophobic solvent (g) and the mixture of residual 1,3 propanediol and hydrophilic solvent (k). (6) Water (m) addition to recover salts and hydrophilic impurities from the hydrophobic solvent. (7) Separation of the two liquid phases of mixed stream (n), to recycle the salts-depleted hydrophobic solvent stream (h) and to remove salts from the process through the aqueous stream (o).

FIG. 4: Method for purifying 1,3-propanediol by adding a hydrophilic less volatile solvent than 1,3-propanediol to mechanically draw out crystallized salts in a falling film or wiped film evaporator, and by eliminating residual traces of pollutants by an optional ion exchange and/or adsorption step: (1) Fermentation clarification (2) Distillation of water (3) Addition of the solvent (4) Evaporation on a falling film or wiped film wherein 1,3-propanediol, light products and a fraction of the heavy products are recovered in the vapour phase where as salts crystallize in the evaporator and are drawn out mechanically at the bottom of the evaporator by solvent flow and scraping (5) Optional ion exchange and/or adsorption step on ion exchange resin, activated charcoal or other adsorbent solids, for removal of residual ionic impurities and/or color-forming impurities (6) Topping (7) Optional ion exchange and/or adsorption step on ion exchange resin, activated charcoal or other adsorbent solids, to remove residual ionic impurities and/or color-forming impurities (8) Stripping (9) Optional ion exchange and/or adsorption step on ion exchange resin, activated charcoal or other adsorbent solids, for removal of residual ionic impurities and/or color-forming impurities.

Figure 1:
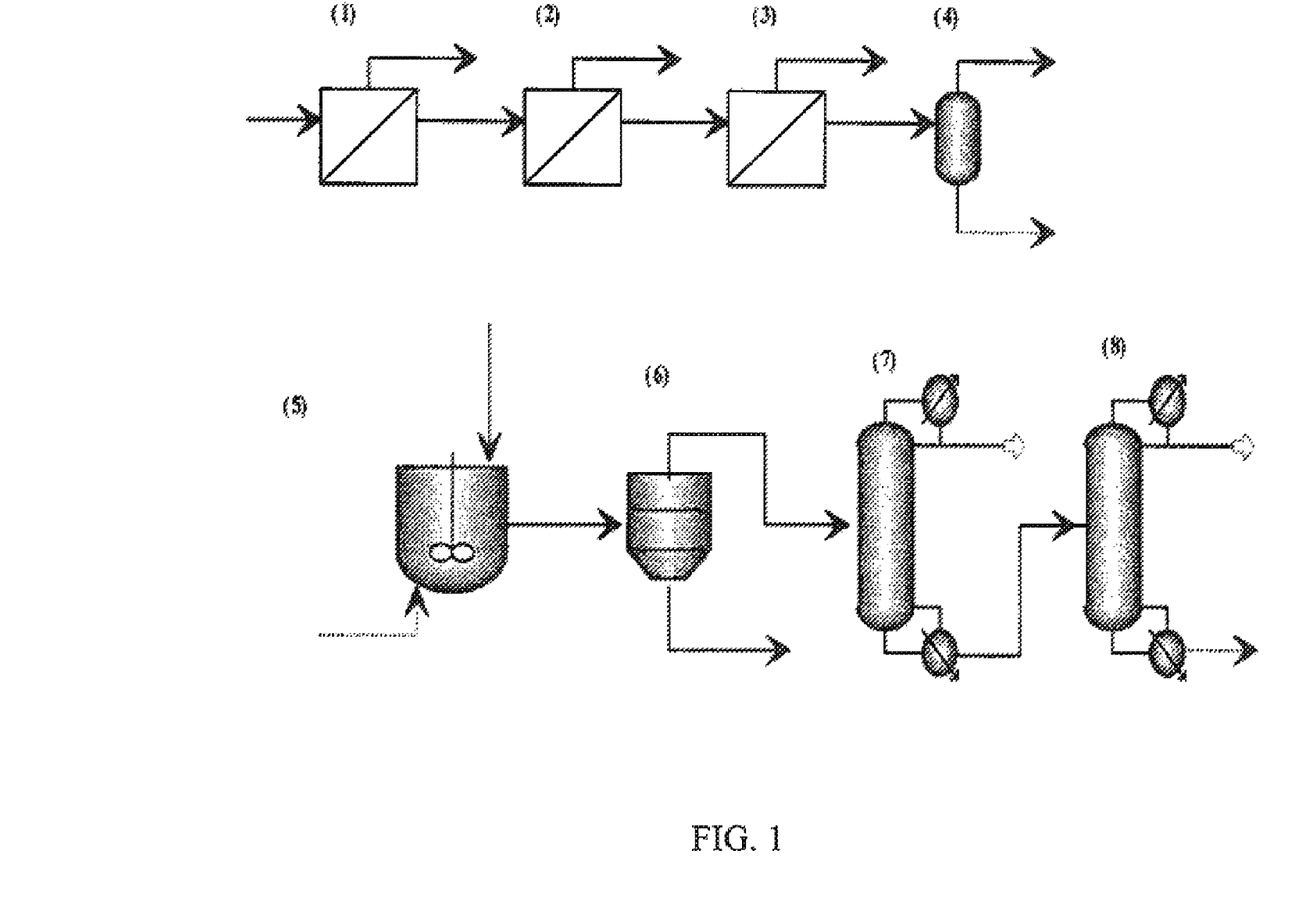
FIG. 1: Method for purifying 1,3-propanediol by adding a less volatile solvent than 1,3-propanediol to mechanically draw out crystallized salts in a falling film or wiped film evaporator. (1) Microfiltration (2) Ultrafiltration (3) Nanofiltration (4) Water evaporation (5) Addition of the solvent (6) Evaporation on a falling film or wiped film wherein 1,3-propanediol, light products and a fraction of the heavy products are recovered in the vapour phase where as salts crystallize in the evaporator and are drawn out mechanically at the bottom of the evaporator by solvent flow and scraping (7) Topping: elimination of light impurities by distillation (8) Stripping: elimination of heavy impurities by distillation.
Figure 2:
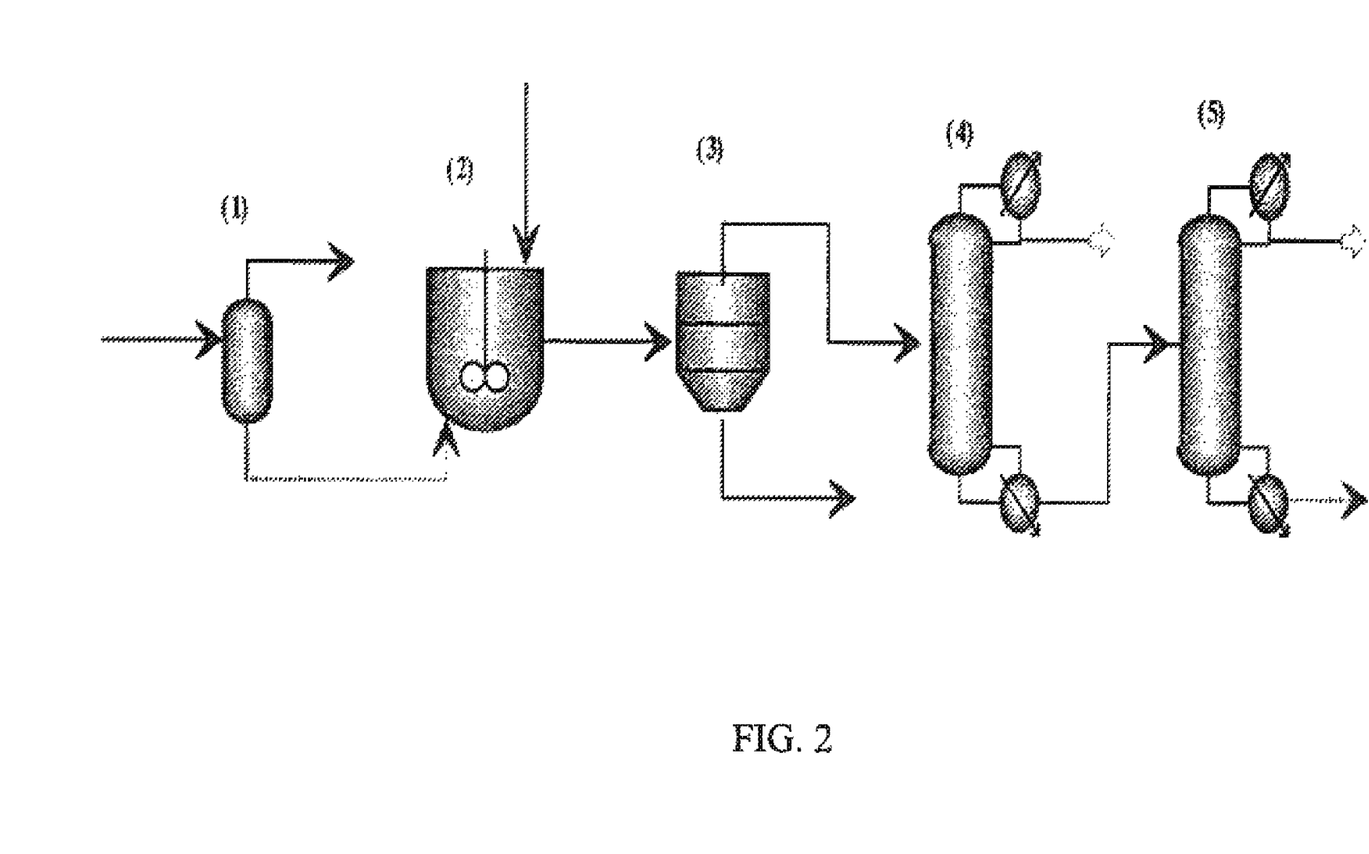
FIG. 2: Method for purifying 1,3-propanediol by adding a less volatile solvent than 1,3-propanediol to mechanically draw out crystallized salts in a falling film or wiped film evaporator: (1) Evaporation of water (2) Addition of the solvent (3) Evaporation on a falling film or wiped film: 1,3-propanediol, light products and a small fraction of the heavy products are recovered in the vapour phase where as salts crystallize in the evaporator and are drawn out mechanically at the bottom of the evaporator by solvent flow and scraping (4) Topping (5) Stripping.
Figure 3:
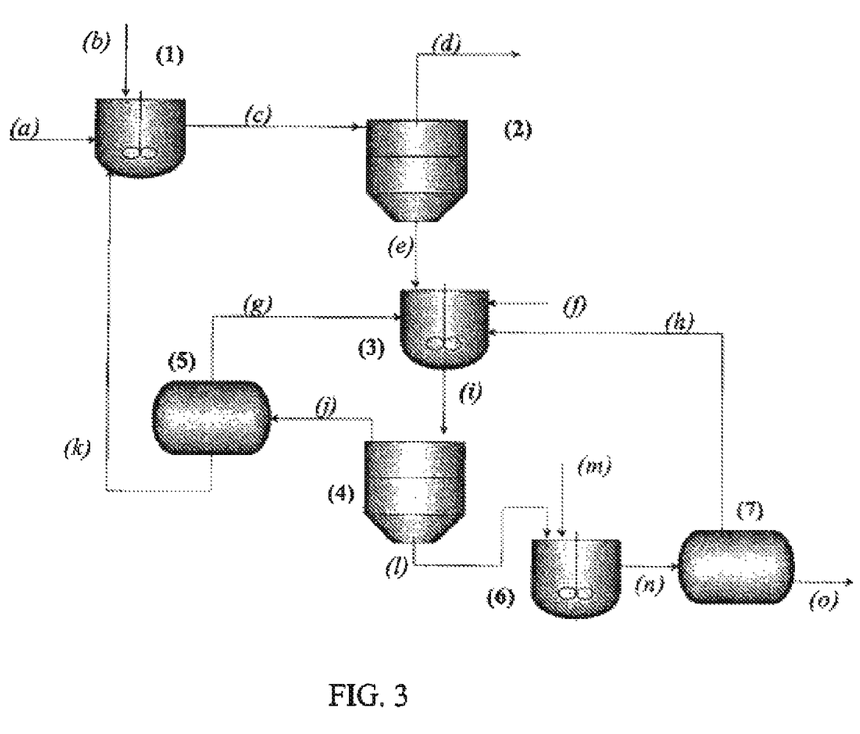
Figure 4:
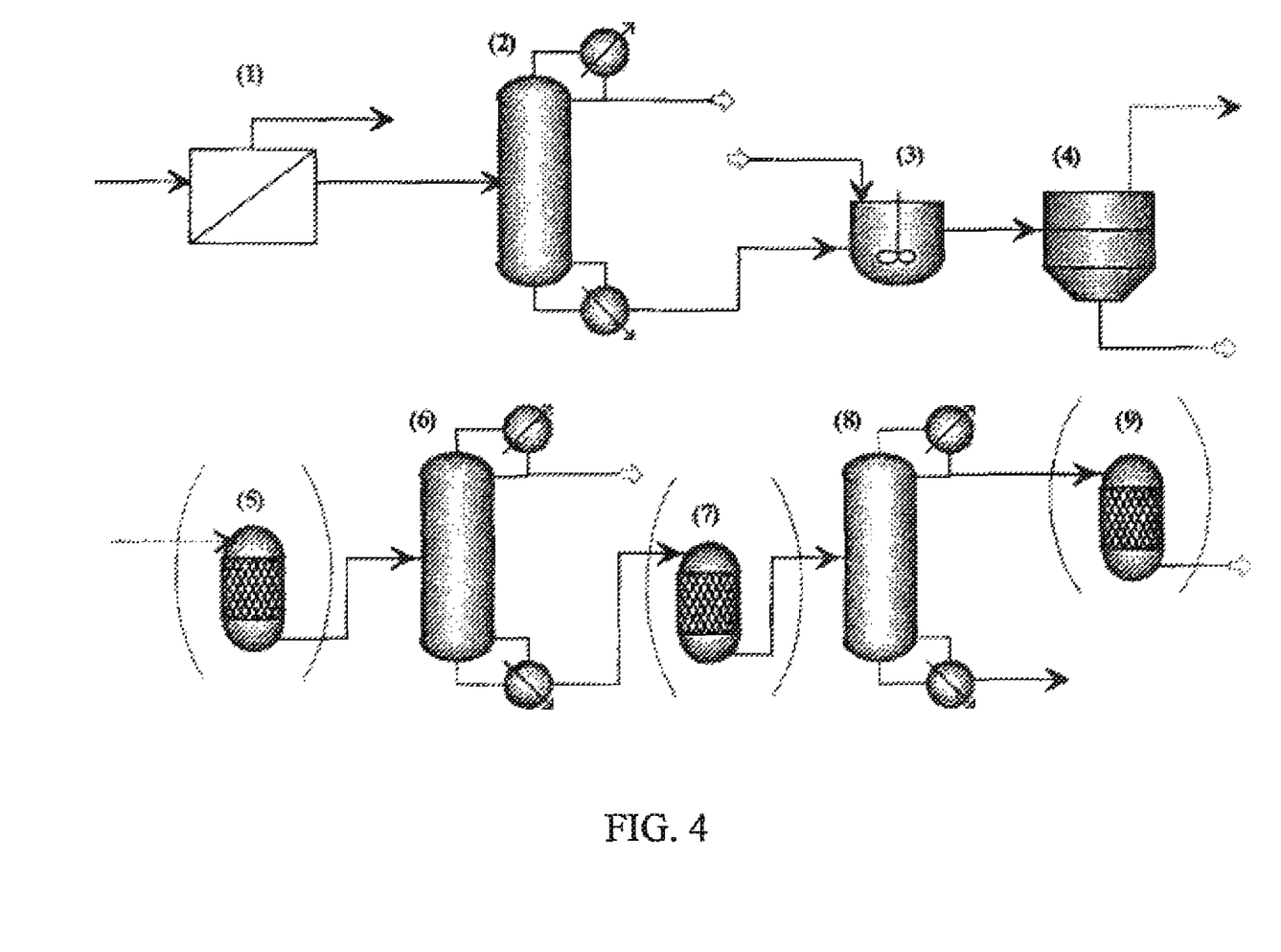

These examples, while indicating preferred embodiments of the invention, are given by way of illustration only.

EXAMPLES

Example 1

A filtered fermentation broth containing 1,3-propanediol (PDO) (A1) was used as a starting material for the following experiments.

Filtration of the fermentation broth comprised the two following steps:
1. 0.22 μm cutoff microfiltration
2. 30 kD cutoff ultrafiltration The ultrafiltration permeate was analyzed by HPLC and results are reported in Table 1.

TABLE 1

Composition of the microfiltered and ultrafiltered PDO fermentation broth (Mixture A1)

| Organic analysis | | Ionic analysis | |
| --- | --- | --- | --- |
| Compound | Concentration g/l | Ion | Concentration g/l |
| Glycerol | 14.4 | Na$^+$ | 2.8 |
| 1,3-propanediol (PDO) | 60.2 | NH$_4^+$ | 6.5 |
| Acetate | 1.2 | K$^+$ | 0.7 |
| Butyrate | 11.2 | Mg$^{2+}$ et Ca$^{2+}$ | <0.1 |
| Lactate | 4.4 | Cl$^-$ | 4.2 |
| Ethanol | 0.6 | SO$_4^{2-}$ | 0.6 |
| | | PO$_4^{3-}$ | 0.6 |
| Water: qs 1L | | | |

The (A1) filtered fermentation broth was first concentrated by evaporation. (A1) Filtered fermentation broth (27 kg) was loaded into a thermosyphon-type evaporator. Operating top pressure was 130 mbar. 71.9 wt % of the solution was evaporated. The water content in the top product was higher than 99 wt %. The PDO fraction in (B1) concentrated mixture was 20.6 wt %. Thus, the PDO yield was 95.8 wt %.

A second evaporation step was operated at a pressure of 40 mbar down to 30 mbar: concentrated product (B1) was heated at a temperature of 40° C. up to 70° C. 3.18 kg of B1 were evaporated. The final evaporated fraction (weight percent of the initial mixture (A1)) was 83.9 wt %. The PDO fraction of the (C1) final concentrated product was 34.0 wt %. Thus, the PDO yield on the second evaporation stage was 95.2 wt %.

Crystallization of salts does not occur at this level of concentration.

Glycerol (310 g) was then added to the (C1) final concentrated product (4.34 kg), to reach a glycerol weight fraction of 15%. Glycerol was purchased from Sigma-Aldrich (99% purity-GC analysis), and used without further purification. The (D1) glycerol-rich mixture obtained was fed to a laboratory wiped thin film evaporator having an internal condenser. The operating pressure was set to 1 mbar. The heating temperature was set to 125° C.

Valuable compounds, including most part of the PDO, were evaporated. Deposit of crystallized salts was prevented by wall scraping of the evaporator and by a continuous flow of glycerol. Salts, heavy compounds and a significant part of the glycerol were collected in the bottom product. The recovered mass of (E1)) distillate was 3.1 kg. PDO weight fraction in (E1) distillate was 42.4%. Thus, PDO yield was 94.7% in the above-described salt elimination step.

Ion analysis results for the (E1) distillate are reported in table 2:

TABLE 2

Quantitative analysis of ionic species in the distillate (E1 mixture)

| | Concentration g/l | |
| --- | --- | --- |
| Ion | Filtered fermentation broth (A1) | Distillate (E1) |
| Na$^+$ | 2.8 | 0.23 to 0.3 |
| K$^+$ | 0.7 | 0.04 to 0.06 |
| Cl$^-$ | 4.2 | 0.4 to 0.5 |
| SO$_4^{2-}$ | 0.6 | 0.04 to 0.007 |
| PO$_4^{3-}$ | 0.6 | 0.03 to 0.05 |
| Mass kg | 27.0 | 3.1 |

Values reported in table 2 confirm that salt elimination efficiency was as high as 99%.

Mixture (E1) was then heated under a pressure of 40 mbar down to 30 mbar. The heating temperature was set at 30-40° C. 36.8 wt % of the solution was evaporated. PDO weight fraction in (F1) residue was 69.0%. Thus, PDO yield was as high as 99%.

Pure PDO (>99.5%-HPLC analysis) was then obtained from the (F1) residue by batch vacuum distillation. The top pressure was set from 1 to 10 mbar, preferably at 5 mbar. The distillation process included the two following steps: light components removal and PDO production. A high reflux ratio during light components removal insured a low PDO fraction in the removed distillate. High reflux ratio during PDO production insured low concentration of heavy components and high PDO purity in the top product. A mass of 930 g of PDO with purity higher than 99.5% (HPLC analysis) was obtained. Thus, batch distillation yield was 68.8%.

Example 2

A filtered fermentation broth containing 1,3-propanediol (PDO) (A2) was used as a starting material for the following experiments. The filtration of the fermentation broth comprised the two following steps:
1. 0.22 μm cutoff microfiltration
2. 30 kD cutoff ultrafiltration The ultrafiltration permeate was analyzed by HPLC and results are reported in Table 3.

TABLE 3

Composition of the microfiltered and ultrafiltered PDO fermentation broth (Mixture A2)

| Organic analysis | | Ionic analysis | |
| --- | --- | --- | --- |
| Compound | Concentration g/l | Ion | Concentration g/l |
| Glycerol | 5.1 | $Na^+$ | 2.3 |
| 1,3-propanediol (PDO) | 60 | $NH_4^+$ | 4.6 |
| Acetate | 1.5 | $K^+$ | 0.6 |
| Butyrate | 12.3 | $Mg^{2+}$ et $Ca^{2+}$ | <0.1 |
| Lactate | 3.5 | $Cl^-$ | 4.3 |
| Ethanol | 0.3 | $SO_4^{2-}$ | 0.5 |
| | | $PO_4^{3-}$ | 0.6 |
| Water: qs 1L | | | |

The (A2) filtered fermentation broth was first concentrated by evaporation. (A2)

Filtered fermentation broth (25 kg) was loaded into a batch evaporator equipped with a rectification column. Operating top pressure was 500 mbar. 85 wt % of the solution was evaporated. The PDO weight fraction of the (B2) concentrated mixture was 39.1%. Thus, the PDO yield was 98%.

Crystallization of salts does not occur at this level of concentration.

Glycerol (760 g) was then added to (B2) concentrated product (3.75 kg), to reach a glycerol weight fraction of 20 wt %. Glycerol was purchased from Sigma-Aldrich (99% purity-GC analysis), and used without further purification. The (C2) glycerol-rich mixture obtained was fed to a laboratory thin film evaporator having an internal condenser. The operating pressure was set to 25 mbar. The wall was heated at a temperature of 170° C. up to 175° C.

Valuable compounds, including most part of PDO, were evaporated. Deposit of crystallized salts was prevented by wall scraping of the evaporator and continuous flow of glycerol. Salts, heavy compounds and some part of glycerol were collected in the bottom product. The mass of recovered distillate (D2) was 3.5 kg. PDO weight fraction in distillate (D2) was 39.7%. Thus, PDO yield was 96.4% on the above-described salt elimination step.

Example 3

The residue leaving the thin-film evaporator during the operation described in example 2 is used as a starting material for the following experiments (A3). That residue is mainly composed of glycerol, salts, and heavy compounds, and it contains the remaining 1,3-propanediol (PDO), which was not evaporated in the operation described in example 2. The composition of that mixture (A3) is described below: Glycerol and PDO weight fractions were determined by HPLC analysis, while salts and heavy compounds weight fractions are estimated based on the initial fermentation broth analysis, and on the various concentration factors of the previous purification steps. It is important to note that a major part of inorganic salts and of heavy impurities (e.g. protein decomposition products) is in the crystallized or precipitated form in mixture (A3). Thus, HPLC analysis results were corrected to obtain the real weight fraction of PDO or Glycerol in the whole mixture.

TABLE 4

Composition of the residue leaving the thin-film evaporator as described in example 2.

| Compound | Concentration % w |
| --- | --- |
| Glycerol | 50% |
| 1,3-propanediol (PDO) | 4% |
| Inorganic salts, either dilute form or crystallized form | 30-35% |
| Heavy compounds (not identified) | q.s. 100% |

A mixture of rapeseed oil methyl esters (RME) was then added to residue (A3), to reach a ratio of 1.5 RME to 1 Residue. The liquid-liquid biphasic mixture obtained (C3) was rigorously mixed and fed to a laboratory thin film evaporator having an internal condenser. The operating pressure was set to 1 mbar. The wall was heated at a temperature of 150° C. up to 155° C. At the end of the operation, a mass of 775 g of mixture (C3) has been fed to the evaporator.

Valuable compounds, Including most part of Glycerol and PDO, were evaporated and obtained in the distillate (D3), as well as the most volatile part of the RME mixture. Distillate (D3) contained hydrophobic RME, which are not miscible in the hydrophilic PDO-Glycerol phase, so the two liquid phases are separated by decantation. The mass of the whole distillate (D3) produced is about 310 g. The light liquid phase obtained by decantation consists in 175 g of RME. The heavy liquid phase obtained by decantation consists in 126 g of a mixture containing 82.7% w of Glycerol and 8.9% w of PDO. Thus, the PDO recovery yield is higher than 90%, while the Glycerol recovery yield is about 67%.

Deposit of crystallized salts was prevented by wall scraping of the evaporator and continuous flow of RME on the wall. Salts, heavy compounds and remaining RME were collected in the bottom product (E3). Water was added in a ratio 3:1 to the bottom product (E3), to recover salts and heavy hydrophilic compounds in an aqueous phase, and recover an almost pure hydrophobic RME phase. The sum of RME masses recovered after both decantation steps represents more than 97% of the initial mass fed to the evaporator. Thus, RME loss due to its solubility in hydrophilic phases is judged negligible.

That operation showed that almost all the PDO is recovered in the heavy phase of the distillate, as well as 70% of the glycerol. Salts and heavy compounds have been transferred to an aqueous stream, which didn't contain any more valuable products and could be wasted. Most part of PDO and Glycerol are recovered in a salts-depleted stream, which could be used as a "heavy solvent" as described in the invention, e.g. to recover PDO from a concentrated fermentation broth.

Example 4

A sample of 1,3-propanediol (PDO) purified by the distillation process described in the invention was used as a starting material for the following experiments. The analysis of that distilled PDO sample showed a purity higher than 99% w, but showed that traces of organic impurities remain, e.g. esters or chlorinated compounds. Those impurities lead to a high residual conductivity and absorbance.

So, ion exchange and adsorption were used as polishing purification techniques to reach higher quality. First, distilled PDO was treated by ion exchange on a mixed-bed ion exchange resin. The ion exchange resin used was purchased from Purolite (Mixed-bed resin MB400—Gel polystyrene crosslinked with divinylbenzene, with functional groups composed of 40% sulphonic acid, and 60% quaternary ammonium), and was rinsed five times before using it. One rinsing consisted in washing the resin during 10 minutes with osmosed water, with a mass ratio water:resin of 4.

Some water is added to the distilled PDO before treating it, to prevent resin degradation: water was added until water weight fraction reached 20%. The treatment is carried out in a batch mode, with a weight fraction of resin in the whole mixture of 19%.

The table below gives the measured conductivity and absorbance of the hydrated PDO as a function of the resin contact time. Operation was carried out in a batch mode, resin and product were vigorously mixed during the operation.

TABLE 5

Conductivity and absorbance of a PDO sample treated by ion exchange.

| Resin contact time (h) | Conductivity (µS/cm) | Absorbance (UV 270 nm) |
|---|---|---|
| 0.0 (initial sample) | 1.3 | 4.6990 |
| 1.0 | 0.3 | 1.9310 |
| 2.0 | 0.2 | 1.2030 |
| 3.0 | 0.2 | 0.8666 |
| 4.0 | 0.2 | 0.6665 |
| 5.0 | 0.2 | 0.3756 |
| 15.0 | 0.2 | 0.1098 |

The decrease of conductivity confirmed that residual ionic impurities which were not eliminated by the distillation process were removed by the ion exchange treatment. The GC analysis confirmed that most of the color-forming organic impurities were eliminated by the ion exchange treatment, too.

The mixture of PDO and water treated by ion exchange is then treated by adsorption on an activated carbon. The activated charcoal was purchased from CECA (GAC 1240), and was used without any preliminary treatment. The adsorption step is carried out in a batch mode, with a weight fraction of activated carbon in the whole mixture of 20%.

The table below gives the measured absorbance of the hydrated PDO as a function of the adsorbents contact time,

TABLE 6

Absorbance of a PDO sample treated by adsorption on activated carbon.

| Resin contact time (h) | Activated carbon contact time (h) | Absorbance (UV 270 nm) |
|---|---|---|
| 5.0 | 0.0 | 0.3756 |
| 5.0 | 4.0 | 0.0139 |
| 5.0 | 7.0 | 0.0020 |
| 15.0 | 0.0 | 0.1098 |
| 15.0 | 4.0 | 0.0042 |
| 15.0 | 7.0 | 0.0020 |

Results above confirmed that in any configuration, ion exchange and adsorption on activated carbon allowed to significantly decreased conductivity and or absorbance of the distilled PDO obtained by the process described in the invention. Thus, ion exchange and adsorption are both relevant techniques to reach a very high purity for the final product.

Example 5

A filtered fermentation broth containing 1,2-propanediol (MPG) (A1)) was used as a starting material for the following experiments.

Filtration of the fermentation broth consisted in a 0.65 µm cutoff microfiltration The microfiltration permeate was analyzed by HPLC and results are reported in Table 7.

TABLE 7

Composition of the microfiltered MPG fermentation broth (Mixture A1)

| Organic analysis | | Ionic analysis | |
|---|---|---|---|
| Compound | Concentration % | Ion | Concentration g/l |
| 1,2 propanediol (MPG) | 4.43 | Na+ | 0.47 |
| Citrate | 0.02 | NH4+ | 4.29 |
| Glucose | 0.05 | K+ | 0.54 |
| Succinate | 0.10 | Mg2+ | 0.09 |
| Glycerol | 0.05 | Ca2+ | 0.02 |
| Acetate | 0.77 | Cl− | 0.05 |
| Hydroxyacetone | 0.31 | SO4− | 4.91 |
| Ethanol | 0.04 | PO4− | 0.40 |
| Pyruvate | 0.17 | | |
| Methylglyoxal | 0.02 | | |
| Water: qs 1L | | | |

The (A1) filtered fermentation broth was first concentrated by evaporation. (A1) Filtered fermentation broth (51.0 kg) was loaded into a thermosyphon-type evaporator. Operating top pressure was 120 mbar. 91.5 wt % of the solution was evaporated. The top product was mainly composed of water, and contained 0.36 wt % of MPG. The MPG fraction in (B1) concentrated mixture was 42.1 wt %. Thus, the MPG yield was 80.8 wt %.

Crystallization of salts does not occur at this level of concentration.

Glycerol was then added to (B1) concentrated product, to reach a glycerol weight fraction of 20 wt %. Glycerol was purchased from Sigma-Aldrich (99% purity-GC analysis), and used without further purification. The (C1) glycerol-rich mixture obtained was fed to a laboratory wiped thin film evaporator having an internal condenser. The operating pressure was set to 50 mbar. The heating temperature was set to 130° C. up to 150° C.

Valuable compounds, including most part of the MPG, were evaporated. Deposit of crystallized salts was prevented by wall scraping of the evaporator and by a continuous flow of glycerol. Salts, heavy compounds and a significant part of the glycerol were collected in the bottom product. The recovered mass of (D1) distillate was 1.06 kg, and the distillate to feed mass ratio was 64.3%. MPG weight fraction in (D1) distillate was 50.8%. Thus, MPG yield was 97.0% in the above-described salt elimination step.

Salts were efficiently removed from the fermentation broth by the above-described evaporation step, as well as heavy insoluble impurities. Distillate (D1) was then treated by successive distillations steps at pressure levels of 10 to 70 mbar, and heating temperatures of 80 to 120° C., to give almost pure MPG. Three samples were produced with a purity higher than 99% (measured by HPLC), without any trace of the impurities reported in Table 7.

REFERENCES

Patent Documents Cited in the Description
EP 1 218 327
U.S. Pat. No. 7,056,439
EP 1 103 618
WO 2004/101479

U.S. Pat. No. 6,361,983
U.S. Pat. No. 5,254,467
WO 2009/068110
US 2004/222153
Non-Patent Literature Cited in the Description
Gong et al., Desalination 191 (2006) 193-199
Gong et al., Desalination 16 1 (2004) 169-178
Zhi-Long Xiu and An-ping Zeng, Appl. Microbiol. Biotechnol., 78:917-926, 2008

The invention claimed is:

1. A method for purifying an alcohol from a fermentation broth, comprising the following steps: a) clarifying the fermentation broth in order to obtain an aqueous solution containing the alcohol, b) adding a solvent to the aqueous solution to reach a proportion of solvent of at least 10% per weight, wherein the solvent has a boiling point which is higher than the boiling point of the alcohol to be purified, c) feeding the aqueous solution containing the solvent to a falling film evaporator, a wiped film evaporator, a thin film evaporator or a short path evaporator, for evaporation of the alcohol to be purified and drawing out of crystallized salts by the solvent, d) recovering the alcohol.

2. A method according to claim 1, wherein the alcohol to be purified from the culture broth is 1,3-propanediol.

3. A method for purifying an alcohol from a fermentation broth according to claim 1, wherein clarification of the fermentation broth in step a) is carried out by filtration.

4. A method for purifying an alcohol from a fermentation broth according to claim 3, wherein filtration consists in successive microfiltration, ultrafiltration and/or nano filtration steps.

5. A method for purifying an alcohol from a fermentation broth according to claim 1, further comprising removal of water from the aqueous solution containing the alcohol obtained in step a).

6. A method for purifying an alcohol from a fermentation broth according to claim 1, wherein in step b) solvent is added to reach a proportion ranging from 10% to 20% by weight of the aqueous solution.

7. A method for purifying an alcohol from a fermentation broth according to claim 1, wherein in step b) the solvent added to the aqueous solution, is glycerol.

8. A method for purifying an alcohol from a fermentation broth according to claim 1, wherein the solvent is a hydrophilic solvent and in step c) an evaporated product containing the alcohol and a bottom product containing hydrophilic solvent, salts and residual alcohol, are obtained.

9. A method for purifying an alcohol from a fermentation broth according to claim 8, wherein the hydrophilic solvent and the residual alcohol contained in the bottom product are recycled.

10. A method for purifying an alcohol from a fermentation broth according to claim 9 wherein recycling of the hydrophilic solvent and of the residual alcohol comprises the following steps: adding a hydrophobic solvent to the bottom product containing hydrophilic solvent, salts and residual alcohol, to reach a proportion of hydrophobic solvent of at least 5% per weight, wherein the hydrophobic solvent has a boiling point which is higher than the boiling point of the hydrophilic solvent; feeding the product of the preceding step to a falling film evaporator, a wiped film evaporator, a thin film evaporator or a short path evaporator, for evaporation of the hydrophilic solvent and of the residual alcohol and drawing out of crystallized salts by the hydrophobic solvent, wherein an evaporated product containing hydrophilic solvent, residual alcohol and hydrophobic solvent is obtained; decanting of the evaporated product to obtain a first phase comprising the hydrophilic solvent and the residual alcohol and a second phase comprising the hydrophobic, solvent;
—recycling of the first phase comprising the hydrophilic solvent and the residual alcohol.

11. A method for purifying an alcohol from a fermentation broth according to claim 10, wherein the hydrophobic solvent is added to reach a proportion ranging from 50% to 200% by weight, of the bottom product.

12. A method for purifying an alcohol from a fermentation broth according to claim 10 wherein the hydrophobic solvent is composed of rapeseed oil methyl esters (RME).

13. A method for purifying an alcohol from a fermentation broth according to claim 1, comprising further purification of the alcohol recovered in step d).

14. A method for purifying an alcohol from a fermentation broth according to claim 13 wherein further purification of the alcohol comprises removing by distillation products and/or azeotropes which have a boiling point lower than that of the alcohol to be purified; and removing by distillation products and/or azeotropes having a boiling point higher than that of the alcohol to be purified.

15. A method for purifying an alcohol from a fermentation broth according to claim 13 wherein further purification of the alcohol comprises removing water by evaporation.

16. A method for purifying an alcohol from a fermentation broth according to anyone of claim 13 wherein further purification of the alcohol comprises ion exchange and/or adsorption.

* * * * *